United States Patent
Provonchee

(10) Patent No.: US 11,691,122 B2
(45) Date of Patent: Jul. 4, 2023

(54) IRRADIATED AGAROSE, COMPOSITIONS THEREOF, AND RELATED METHODS

(71) Applicant: Advanced Aesthetic Technologies, Inc., Brookline, MA (US)

(72) Inventor: Richard Provonchee, Cushing, ME (US)

(73) Assignee: Advanced Aesthetic Technologies, Inc.

( * ) Notice: Subject to any disclaimer, the term of this patent is extended or adjusted under 35 U.S.C. 154(b) by 501 days.

(21) Appl. No.: 16/665,084

(22) Filed: Oct. 28, 2019

(65) Prior Publication Data

US 2020/0139347 A1 May 7, 2020

Related U.S. Application Data

(60) Provisional application No. 62/754,813, filed on Nov. 2, 2018.

(51) Int. Cl.
*A61K 9/00* (2006.01)
*B01J 20/291* (2006.01)
*B01J 20/22* (2006.01)

(52) U.S. Cl.
CPC ............. *B01J 20/291* (2013.01); *B01J 20/22* (2013.01)

(58) Field of Classification Search
CPC .. A61K 9/0087; A61K 9/1682; A61K 9/2086; A61K 9/3101; A61L 13/00
See application file for complete search history.

(56) References Cited

U.S. PATENT DOCUMENTS

| | | | |
|---|---|---|---|
| 4,983,268 A | 1/1991 | Kirkpatrick et al. | |
| 5,143,646 A * | 9/1992 | Nochumson | C08L 5/12 516/107 |
| 5,230,832 A | 7/1993 | Perlman | |
| 2008/0081056 A1 * | 4/2008 | Nussinovitch | A61K 8/9767 424/401 |
| 2010/0075391 A1 | 3/2010 | Watling et al. | |
| 2018/0000989 A1 | 1/2018 | Nazhat et al. | |

FOREIGN PATENT DOCUMENTS

WO 2018026400 A1 4/2017
WO WO-2018026400 A1 * 2/2018 ......... A61F 13/00063

OTHER PUBLICATIONS

Aliste et al. (Radiation effects on agar, alginates and carrageenan to be used as food additives; Radiation Physics and Chemistry 2000, 305-308) (Year: 2000).*
Fernando A. Osorio, "Effects of Concentration, Bloom Degree, and pH on Gelatin Melting and Gelling Temperatures Using Small Amplitude Oscillatory Rheology", Journal, 2007, 841-851, International Journal of Food Properties, vol. 10.
Sun et al. "Light Microscopy of the Structure of a Gel." J. Struct. Biol. 113.1(1994): 56-63.

* cited by examiner

*Primary Examiner* — Micah Paul Young
(74) *Attorney, Agent, or Firm* — Womble Bond Dickinson (US) LLP; Deborah M. Vernon

(57) ABSTRACT

Irradiated agarose gels and compositions containing irradiated agarose gels are described, along with methods of production and use. Methods of forming an irradiated agarose composition include irradiating an agarose in dry form to produce an irradiated agarose, dissolving the irradiated agarose in a solvent to form a solution containing irradiated agarose, and gelling the solution containing irradiated agarose to form a gel containing irradiated agarose. The resulting gel containing irradiated agarose may have a reduced gel strength, making it more suitable for use as an injectable, even at high concentrations.

11 Claims, 1 Drawing Sheet

Method 200

```
Irradiate an agarose in dry form to produce an
irradiated agarose
202
           │
           ▼
Dissolve the irradiated agarose in a solvent
204
           │
           ▼
Gel the solution containing irradiated agarose to form
a gel made from irradiated agarose
206
           │
           ▼
Optionally fracture the gel made from irradiated
agarose
208
           │
           ▼
Optionally administer the gel made from irradiated
agarose to a patient
210
```

IRRADIATED AGAROSE, COMPOSITIONS THEREOF, AND RELATED METHODS

CROSS-REFERENCE TO RELATED APPLICATIONS

This application claims priority from U.S. Provisional Application Ser. No. 62/754,813, titled "Irradiated Agarose, Compositions Thereof, and Related Methods" filed Nov. 2, 2018, the contents of which are incorporated by reference herein.

BACKGROUND

Agarose is a linear polysaccharide polymer made up of repeating units of agarobiose, which is a disaccharide formed of D-galactose and 3,6-anhydro-L-galactopyranose. Agarose is one of the two principal components of agar and is purified from agar by removing agar's other component, agaropectin. Agarose is frequently used in molecular biology for the separation of large molecules, especially DNA, by electrophoresis.

SUMMARY

This disclosure relates to gels containing irradiated agarose and compositions containing irradiated agarose, as well as related methods of production and use. In some embodiments, a method of forming a composition containing irradiated agarose is disclosed and the method includes irradiating an agarose in dry form to produce an irradiated agarose, dissolving the irradiated agarose in a solvent to form a solution containing irradiated agarose, and gelling the solution containing irradiated agarose to form a gel containing irradiated agarose. The agarose may be irradiated in dry form with at least 5 kilograys (kGy) of radiation or with at least 40 kilograys (kGy) of radiation, in some embodiments. In these and other embodiments, water may be used as the solvent and the solution may contain between 3% and 10% irradiated agarose by weight. The solution may be gelled by chemical cross-linking or cooling, in some embodiments. The gel containing irradiated agarose may have an agarose concentration of at least 3% or at least 5%, in select embodiments. In these and other embodiments, the gel containing irradiated agarose may have a gel strength of less than 2,000 gm/cm$^2$. The gel containing irradiated agarose need not be irradiated while in gel form. The gel containing irradiated agarose may be administered to a patient, for example via injection. In some embodiments, the gel may be fractured prior to being administered.

BRIEF DESCRIPTION OF THE DRAWINGS

FIG. 1 illustrates an exemplary method of forming a gel made from irradiated agarose, in accordance with various embodiments of the subject disclosure.

DETAILED DESCRIPTION

This disclosure relates to irradiated agarose compositions for dermal filling and other related applications. Gamma radiation has previously been used to sterilize various compositions and devices. However, in contrast to using gamma radiation as a terminal (end of process) sterilization step, the present disclosure describes methods and compositions in which agarose is irradiated in dry form and then subsequently prepared for insertion into the body. As described in more detail below, gels and other articles formed from the disclosed irradiated agarose may be used for any purpose, including cosmetic, reconstructive, and/or therapeutic applications.

Irradiating an agarose in gel form can negatively impact the gel and lessen its shelf life. However, irradiating an agarose in dry form (prior to forming a gel) can advantageously avoid the negative effects of irradiating the gel and may also positively impact the properties of a gel formed from the irradiated agarose. For example, a gel containing agarose that was irradiated in dry form may have modified elastic modulus (G') and viscous modulus (G") rheological properties as well as a lower gel strength as compared to a gel containing agarose that has not been irradiated.

FIG. 1 illustrates an exemplary method 200 of preparing an irradiated agarose in accordance with the subject disclosure. As shown in FIG. 1, method 200 includes irradiating an agarose in dry form to produce an irradiated agarose (block 202). As will be appreciated by those skilled in the art, agarose may exist in various forms, including in dehydrated or dry forms, dissolved in a liquid, or as a gel. The term "agarose in dry form" as used herein, refers to agarose with little or no water present. Generally, this means the agarose is dry but also includes agaroses in the presence of a non-aqueous liquid. This liquid can be either a solvent or non-solvent for the agarose or combination thereof. This liquid may be, for example, glycerin or a glycol, for example, propylene glycol, or an alcohol. As used herein, the term "dry" or "in dry form" refers to an agarose that has less than 25% water content by weight. In some cases, an agarose in dry form includes less than 20%, 10%, 8%, 6%, 5%, 4%, 3%, 2%, or 1% water content by weight.

As will be appreciated, a "dry" agarose or an agarose "in dry form" may refer to various types of agarose structures. For example, a dry agarose may take the form of a solid, particles, powder, thread, film, and/or matrix. The agarose in dry form that is irradiated may be, for example, in the form of a powder as commonly supplied commercially, or in the form of a dehydrated or partially dehydrated gel, or in the form of an agarose precipitated from a glycol, or some combination thereof. Suitable precipitation techniques are known to those skilled in the art.

The agarose in dry form that is irradiated may be modified (i.e., derivatized) or unmodified. As will be understood by those skilled in the art, modified or derivatized agarose may have slightly or significantly different properties as opposed to unmodified agarose (e.g., gel strength, melting/gelling point, molecular weight, viscosity, etc.). As used herein, the term "agarose" refers to a compound based on the following polymeric structure:

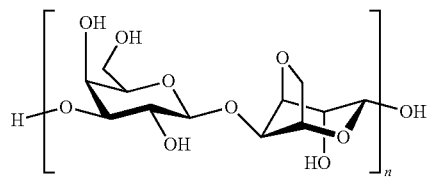

The agarose used in the disclosed methods and compositions may be commercially obtained or prepared by a user. The disclosed agarose may, in some embodiments, include one or more crude, purified, derivatized or modified agars or agaroses. For example, in certain embodiments, the agarose is selected from agarose, purified agarose, modified agarose, and/or derivatized agarose. The agarose may also be used as mixtures with other compatible polymers and additives such as agar, carrageenan, chitosan, alginate, gelatin, hyaluronic acid, and/or collagen. In select embodiments, the agarose is unmodified or modified agarose, and/or derivatized agarose. In certain embodiments, the agarose is Gracilaria-derived agarose. Gracilaria-derived agarose has a higher methoxy content than agarose derived from other sources (e.g., Gelidium). Agaroses from other seaweeds, for example, Pterocladia or Gelidiella may also be used as the disclosed agarose.

The agarose in dry form may be irradiated using any suitable technique, such as processes that employ gamma radiation, x-ray or beta radiation (e.g., electron beam "e-beam" processing). Numerous types of irradiating devices are known in the art and may be used to irradiate agarose in dry form in accordance with the disclosed methods. The agarose in dry form may be irradiated with any suitable amount of radiation, depending on the desired specifications of the resulting irradiated agarose. For example, in some embodiments, the agarose may be dosed with at least 5 kilograys (kGy), 10 kGy, 20 kGy, 30 kGy, 40 kGy, 50 kGy, 60 kGy, 70 kGy, 80 kGy, 90 kGy, 100 kGy, or more. In select embodiments, the agarose is irradiated with between 10 and 100 kGy, between 20 and 80 kGy, or between 40 and 60 kGy. The gel strength and viscosity of the resulting agarose may be tailored by simply adjusting the irradiation dosage of the agarose in dry form.

Among other possible effects, irradiating an agarose in dry form may, in some cases, reduce its molecular weight. Without wishing to be bound by theory, irradiating an agarose in dry form may cleave molecular bonds of the agarose structure, thereby reducing the total molecular weight of the agarose. Additionally, in some embodiments, irradiating an agarose in dry form may reduce viscosity and/or gel strength of the resulting agarose. In select embodiments, irradiating an agarose in dry form may reduce the viscosity of the resulting agarose by at least 5%, 10%, 20%, 30%, 40%, 50%, or more. In these and other embodiments, irradiating the agarose in dry form may reduce the gel strength of the resulting agarose gel by at least 5%, 10%, 20%, 30%, 40%, 50%, or more. For example, in some embodiments, irradiating the agarose in dry form may reduce the gel strength of the resulting agarose gel to less than 10%, 20%, 40% or less than 80% of the gel strength of a gel made with the un-irradiated agarose. If a high enough radiation dose is applied to the agarose in dry form, the resulting agarose may not even gel at all. Such an agarose could be useful in applications by itself or in combination with gelled agarose.

Method 200 of FIG. 1 continues with dissolving the irradiated agarose in a solvent (block 204). Any suitable solvent may be used to dissolve the irradiated agarose. For example, in some embodiments, the irradiated agarose may be dissolved in water with or without non-aqueous liquid(s) present. In some embodiments, the irradiated agarose may be dissolved in a non-aqueous solvent. This solvent may be, for example, glycerin or a glycol, for example, propylene glycol or combinations thereof. Suitable solvents and techniques are known and would be available for use by one skilled in the relevant art. In some embodiments, the irradiated agarose may be dissolved in sufficient solvent to produce a solution with at least 1%, 3%, 5%, 10%, 12%, 15% or more irradiated agarose by weight. In these and other embodiments, a solution having between 1% and 15%, between 3% and 10%, or approximately 5% irradiated agarose by weight may be prepared. In some embodiments, the solvent may be heated to facilitate dissolution of the irradiated agarose. If appropriate for the intended application, one or more additives may also be added to the solution containing irradiated agarose.

Method 200 of FIG. 1 continues with gelling the solution containing irradiated agarose to form a gel made from irradiated agarose (block 206). The irradiated agarose may be gelled according to any known technique, including chemical cross-linking. For example, a solution containing irradiated agarose may be poured into a mold or other casting device. The mold or casting device may then be kept stationary or relatively stationary while the gel sets and forms. In some embodiments, the irradiated agarose may be gelled at a room temperature, or a temperature slightly higher or slightly lower than room temperature. After gelling, the agarose gel may have an agarose concentration of at least 0.1%, 1%, 3%, 5%, 7%, 10%, 12%, 15%, or more by weight. In some embodiments, if for example, the irradiated agarose has been dissolved in a non-aqueous solvent, it will not gel until exposed to water. In some embodiments, if for example, the irradiated agarose was precipitated from a glycol solution, it will dissolve and gel on exposure to water at room temperature.

Method 200 of FIG. 1 continues with optionally fracturing the gel made from irradiated agarose (block 208). Suitable fracturing techniques are known to those skilled in the art. Example fracturing techniques include, but are not limited to, forcing a gel through a screen or one or more apertures to reduce the particle size of the gel. As will be appreciated by those skilled in the art upon consideration of the subject disclosure, fracturing the gel made from irradiated agarose (if desired) may reduce the particle size of the gel, reduce its water content, and/or facilitate mixing if the gel contains one or more additives. In some cases, fracturing the gel may also facilitate delivery of the gel through a needle or other bored device. In addition to these benefits, using irradiated agarose may also permit fracturing and use of formulations with higher agarose concentrations. For example, formulations with a high agarose concentration generally have a high gel strength, which makes fracturing difficult or impossible. Irradiating the agarose (either in dry form or in solution) reduces its gel strength and makes it possible for a formulation with a high agarose concentration to be fractured.

Method 200 of FIG. 1 concludes with optionally administering the gel made from irradiated agarose to a patient (block 210). In some embodiments, the gel made from irradiated agarose is administered to a patient transdermally via a needle. In some such embodiments, the gel made from irradiated agarose may be prepared for use by an aseptic fill process (e.g., a process in which the agarose gel is loaded into a delivery device in a sterile manner). In embodiments in which an aseptic fill process is used, there may be no need for a terminal sterilization step to occur in which the gel made from irradiated agarose is sterilized after at least some packaging has taken place. The delivery technique can be selected based on the intended use of the gel made from irradiated agarose. In select embodiments, the gel made from irradiated agarose may be used for dermal fill, reconstruction, and/or scaffolding applications. In select embodiments, the disclosed agarose compositions are used for one or more of the following: filling in wrinkles, fine lines, or deep creases, improving skin imperfections, such as scars, adding volume to lips or cheeks, contouring the jaw line, or adjusting the appearance of any other body part, such as rhinoplasty. In addition to uses as an injectable, the disclosed agarose compositions may also be used topically, in some embodiments. For example, the agarose compositions may, in some cases, be used in wound care applications for skin or be used to deliver agents topically. In select embodiments, the disclosed agarose compositions may even be appropriate for use in the eye or in mucosal membranes. Countless other uses for the disclosed gels or compositions containing irradiated agarose are possible and contemplated herein.

In some embodiments, the disclosed agarose gel compositions are administered to a patient at concentrations of at least 2%, 3%, 4%, 5%, 6%, 7%, 8%, 9%, or 10% by weight. In these and other embodiments, the gel made from irradiated agarose may be mixed with other types of agaroses (e.g., agaroses having a different melting point and/or gel strength than the gel formed from agarose irradiated in dry form). Agarose compositions having varying properties can be produced by mixing agaroses prepared according to different techniques (e.g., agaroses irradiated in dry form with different dosings, or agarose irradiated in dry form mixed with agarose that was not irradiated in dry form).

Although method 200 outlines possible steps for producing and using a gel made from irradiated agarose, other methods of production and use are also possible. For example, agarose irradiated in dry form may be utilized by simply exposing it to water. Depending on the form of the irradiated agarose, when exposed to water, it may form a gel, or it may swell or rehydrate to some extent, or both. In some such embodiments, the agarose may be irradiated in dry form as a film, powder, thread, or matrix and may then be applied to a patient without further substantive processing.

EXAMPLES

In a first experimental example, two 3.5% agarose gels (3.5 grams agarose in 100 ml H$_2$O) were made. The first gel (#1) was made with P.F.G.E agarose Scientific) that had not been exposed to gamma irradiation. The second gel (#2) was made with P.F.G.E agarose (IBI Scientific) that had been exposed to 25 kGy gamma irradiation. Gel #1 had a gel strength of 5200 gm/cm$^2$ and gel #2 had a gel strength of 1920 gm/cm$^2$.

In a second experimental example, two 1 ml syringes were fitted with 180 mesh screens such that the contents of the syringe needed to pass through the screen on delivery. The first syringe (#1) was loaded with a 3.5% solution of un-irradiated P.F.G.E agarose and the second syringe (#2) was loaded with a solution of 3.5% P.F.G.E agarose made with agarose powder that had been exposed to 25 kGy gamma irradiation. The solution in both syringes was allowed to cool and form a gel.

It was impossible to force the gel from syringe #1 through the 180 mesh. The plunger of the syringe bent before enough pressure could be applied to express the gel through the screen. The gel in syringe #2 could be easily expressed through the 180 mesh screen requiring a force of less than 20 Newton on the plunger.

The disclosed techniques and compositions may provide numerous advantages over alternative preparation and sterilization procedures. Notably, irradiating an agarose while in dry form as opposed to in gel form may result in unique properties of the resulting agarose. Specifically, an agarose having reduced molecular weight, reduced gel strength, and/or reduced viscosity may be obtained by irradiating the agarose in dry form. Additionally, agarose gels prepared according to the disclosed methods may also have improved tactile effects in the body. For example, the disclosed agarose gels (formed from agarose irradiated in dry form) may be less brittle and softer than conventional agarose gels. Due to the nature of the presently disclosed agarose gels, agarose gels with higher agarose concentrations may be appropriate for administration to a patient, which may increase the overall residence time in the body and may also increase the time needed before follow-up procedures to replenish gel that is consumed by the body.

The features and advantages described herein are not all-inclusive and, in particular, many additional features and advantages will be apparent to one of ordinary skill in the art in view of the present disclosure. Persons skilled in the relevant art can appreciate that many modifications and variations are possible in light of the above disclosure.

The invention claimed is:

1. A method of forming an irradiated agarose composition, the
    method comprising: irradiating an agarose in dry powder form to produce an irradiated agarose, wherein the agarose is irradiated in dry form with at least 5 kilograys (kGy) of radiation;
    dissolving the irradiated agarose in a solvent to form a solution containing irradiated agarose; and
    gelling the solution containing irradiated agarose to form a gel containing irradiated agarose, wherein the solvent is water and the solution contains between 3% and 10% irradiated agarose by weight.

2. The method of claim 1, wherein the agarose is irradiated in dry form with at least 40 kilograys (kGy) of radiation.

3. The method of claim 1, wherein gelling the solution is accomplished by chemical cross-linking or cooling.

4. The method of claim 1, wherein the gel containing irradiated agarose has an agarose concentration of at least 3%.

5. The method of claim 1, wherein the gel containing irradiated agarose has an agarose concentration of at least 5%.

6. The method of claim 4, wherein the gel containing irradiated agarose has a gel strength of less than 2,000 gm/cm$^2$.

7. The method of claim 1 further comprising administering the gel containing irradiated agarose to a patient.

8. The method of claim 7 further comprising fracturing the gel containing irradiated agarose prior to administering the gel to the patient.

9. The method of claim 8, wherein the gel containing irradiated agarose is administered to a patient via injection.

10. A composition comprising the gel containing irradiated agarose of claim 1.

11. The method of claim 1 further comprising precipitating agarose from a glycol solution to produce the agarose in dry form.

* * * * *